US008575309B2

(12) United States Patent
Polt et al.

(10) Patent No.: US 8,575,309 B2
(45) Date of Patent: Nov. 5, 2013

(54) DELTA-OPIOID RECEPTOR SELECTIVE ANALGESICS

(75) Inventors: Robin Polt, Lexington, MA (US);
Edward J. Bilsky, Lexington, MA (US)

(73) Assignee: Biousian Biosystems, Inc., Lexington, MA (US)

( * ) Notice: Subject to any disclaimer, the term of this patent is extended or adjusted under 35 U.S.C. 154(b) by 0 days.

(21) Appl. No.: 13/133,266

(22) PCT Filed: Dec. 8, 2009

(86) PCT No.: PCT/US2009/006436
§ 371 (c)(1),
(2), (4) Date: Aug. 25, 2011

(87) PCT Pub. No.: WO2010/090628
PCT Pub. Date: Aug. 12, 2010

(65) Prior Publication Data
US 2012/0101043 A1    Apr. 26, 2012

Related U.S. Application Data

(60) Provisional application No. 61/201,159, filed on Dec. 8, 2008, provisional application No. 61/277,279, filed on Sep. 23, 2009.

(51) Int. Cl.
| A61K 38/08 | (2006.01) |
| C07K 7/00 | (2006.01) |
| C07K 9/00 | (2006.01) |
| C07K 19/00 | (2006.01) |

(52) U.S. Cl.
USPC ............ 530/329; 530/302; 514/21.7; 514/25; 514/17.7

(58) Field of Classification Search
None
See application file for complete search history.

(56) References Cited

U.S. PATENT DOCUMENTS

2007/0093420 A1    4/2007    Yeomans et al.

OTHER PUBLICATIONS

Tomatis et al., Synthesis and pharmacological activity of deltorphin and dermorphin-related glycopeptides. J Med Chem. Aug. 29, 1997;40(18):2948-52.*
Elmagbari et al., Antinociceptive structure-activity studies with enkephalin-based opioid glycopeptides. J Pharmacol Exp Ther. Oct. 2004;311(1):290-7. Epub May 27, 2004.*
Bilsky et al., "Enkephalin Glycopeptide Analogues Produce Analgesia with Reduced Dependence Liability," J. Med. Chem, 2006, vol. 43, pp. 2586-2590.
Egleton et al., "Biousian Glycopeptides Penetrate the Blood-brain Barrier," Tetrahedron:Asymmetry, 2005, vol. 16, pp. 65-75.
Erspamer et al., "Deltorphins: A Family of Naturally Occurring Peptides with High Affinity and Selectivity for δ Opioid Binding Sites," PNAS USA, 1989, vol. 86, pp. 5188-5192.
Kane et al., "Molecular Recognition of Opioid Receptor Ligands," AAPS J., 2006, vol. 8, pp. E126-E137.
Kane et al., "A Unique Binding Epitope for Salvinorin A, a Non-nitrogenous Kappa Opioid Receptor Agonist," FEBS J., 2006, vol. 273, pp. 1966-1974.

(Continued)

*Primary Examiner* — Jeffrey Stucker
*Assistant Examiner* — Aurora M Fontainhas
(74) *Attorney, Agent, or Firm* — K&L Gates LLP; John M. Garvey

(57) ABSTRACT

Methods and materials are provided for the production of glycosylated peptides that exhibit high affinity and specificity for delta opioid receptors. The methods and materials of the present invention may be used for treatment of conditions involving pain, such as acute pain and nociceptic pain, neuralgia and myalgia.

11 Claims, 6 Drawing Sheets

(56) References Cited

OTHER PUBLICATIONS

Lazarus et al., "What Peptides These Deltorphins Be?" Progress in Neurobiology, 1999, vol. 57, pp. 377-420.

Middleton et al., "Highly Potent and Selective Zwitterionic Agonists of the b-opioid Receptor. Part 1," Bioorganic and Medicinal Chemistry Letters, 2006, vol. 16, pp. 905-910.

Negri et al., "Dermorphin and Deltorphin Glycosylated Analogues: Synthesis and Antinociceptive Activity after Systemic Administration," J. Med. Chem., 1999, vol. 42, pp. 400-404.

Amiche et al., "Dermenkephalin (Tyr-D-Met_Phe-His-Leu-Met-Asp-NH2): a potent and fully specific agonist for the delta opioid receptor," Mol Pharmacol. 1989, vol. 35, No. 6, pp. 774-779.

Egleton et al., "Improved blood-brain barrier penetration and enhanced analgesia of an opioid peptide by glycosylation," J Pharmacol Exp Ther., 2001, vol. 299, No. 3, pp. 967-972.

Polt et al., "Glycosylated Neuropeptides: A New Vista for Neuropsychopharmacology?" Med Res Rev., 2005, vol. 25, No. 5, pp. 557-585.

Feldman, "Tail Flick Assay, Animal Models of Diabetic Complications Consortium," AMDCC Protocols, 2004 [Retrieved from the Internet on Oct. 26, 2010:<URL: http://www.diacomp.org/shared/showFile.aspx?doctypeid=3&docid=34>].

International Search Report and Written Opinion (PCT/US09/06436); Date of Mailing: Nov. 4, 2010, 6 pages.

* cited by examiner

FIGURE 1 = DELTA BINDING

FIGURE 2  Mu Binding

FIGURE 4
NOVEL VARIANT/GLYCOSYLATED PEPTIDE SEQUENCES

| Sequence | BB# | Mol.Wt (TFA salt) | % Purity | % Inhibition at δ 100 nM, 1μM | % Inhibition at μ 100 nM, 1μM | Ki δ (nM) | Ki μ (nM) | GTPγS δ | GTPγS μ | Comments |
|---|---|---|---|---|---|---|---|---|---|---|
| DPDPE | | | | 72, 84 | 23, 62 | 4.3 | 180 | | | 1:42 DOR:MOR |
| H₂N-YaFDVVGS(beta-D-Glc)-G-amide | LSZ-27 | 1074 (1189) | ~98 | 51, 67 | 6, 48 | 33 | 570 | | | 1:17 DOR:MOR |
| H₂N-YmFHLMS(beta-D-Glc)-amide | BBI-11001 | 1089 (1203) | >95 | 72, 84 | 63, 89 | | | | | |
| H₂N-YaFHLAS(beta-D-Glc)-amide | BBI-11002 | 970 (1083) | >95 | 55, 77 | 82, 97 | | | | | |
| H₂N-YmFHLMT(beta-D-Glc)-amide | BBI-11003 | 1104 (1217) | >95 | 75, 83 | 57, 89 | | | | | |
| H₂N-YaFHLAT(beta-D-Glc)-amide | BBI-11004 | 984 (1097) | >95 | 61, 76 | 88, 98 | | | | | |
| H₂N-YaFE-Nva-Nva-S(beta-D-Glc)-amide | BBI-11005 | 976 (1089) | >95 | 65, 80 | 11, 44 | 20 | 710 | | | 1:36 DOR:MOR |
| H₂N-YaFE-Nle-Nle-S(beta-D-Glc)-amide | BBI-11006 | 1004 (1117) | >95 | 66, 81 | 7, 42 | | | | | |
| H₂N-YaFE-Nva-Nva-T(beta-D-Glc)-amide | BBI-11007 | 990 (1103) | >95 | 64, 80 | 13, 36 | | | | | |
| H₂N-YaFE-Nle-Nle-T(beta-D-Glc)-amide | BBI-11008 | 1017 (1131) | >95 | 74, 84 | 7, 37 | 14 | 1100 | | | 1:79 DOR:MOR |
| H₂N-YaFE-Nle-Nle-T-amide | BBI-11009 | | | | | | | | | Unglycosylated control |
| H₂N-YaFE-Nle-Nle-t(beta-D-Glc)-amide | BBI-11010 | | | | | | | | | D-threonine Glycoside |
| H₂N-YaFE-Nle-Nle-s(beta-D-Glc)-amide | BBI-11011 | | | | | | | | | D-serine Glycoside |
| H₂N-YaFE-Nle-Nle-T(beta-D-Rhamnoside)-amide | BBI-11012 | | | | | | | | | More Lipophilic Sugar |
| H₂N-YaFE-Nle-Nle-T(beta-Lactoside)-amide | BBI-11013 | | | | | | | | | More Hydrophilic Sugar |
| H₂N-YaFEβt-T(beta-D-Glc)-amide | BBI-11014 | | | | | | | | | |
| H₂N-YaFEVV-S(beta-D-Glc)-amide | BBI-11015 | | | | | | | | | |
| H₂N-Dmt-aFE-Nle-Nle-T(beta-D-Glc)-amide | BBI-11016 | | | | | | | | | |
| H₂N-Ya-Tic-E-Nle-Nle-T(beta-D-Glc)-amide | BBI-11017 | | | | | | | | | |
| H₂N-YBFE-Nle-Nle-T(beta-D-Glc)-amide | BBI-11018 | | | | | | | | | |
| H₂N-Tmt-aFE-Nle-Nle-T(beta-D-Glc)-amide | BBI-11019 | | | | | | | | | |
| H₂N-Ya-Nmf-E-Nle-Nle-T(beta-D-Glc)-amide | BBI-11020 | | | | | | | | | |
| H₂N-YaFE-Nle-Nle-Ser(beta-Lactoside)-amide | BBI-11021 | | | | | | | | | |
| H₂N-YaFEVV-Ser(beta-Lac)-amide | BBI-11022 | | | | | | | | | |

Dmt = 2,6-dimethyltyrosine;
B = alpha-aminoisobutyric acid
Nmf = N-methylphenylalanine Tic = tetrahydroisoquinoline-3-carboxylic acid
Tmt = 2,5,beta-trimethyltyrosine (R,S isomer)
Nva = L-norvaline Nle = L-norleucine

FIGURE 5
Figure 5a
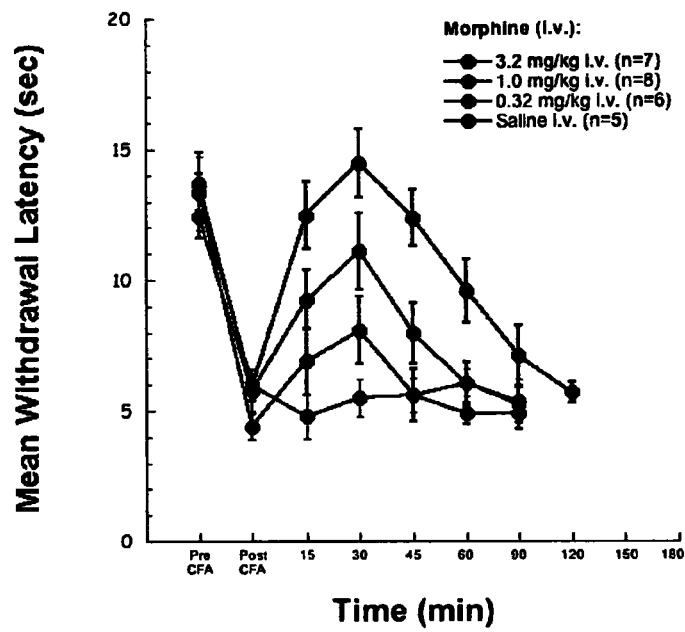
Figure 5b
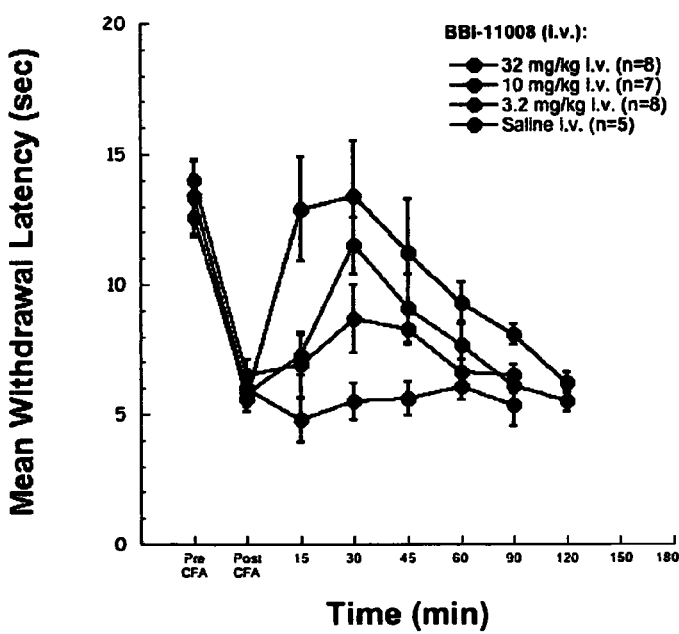

FIGURE 6
Figure 6a
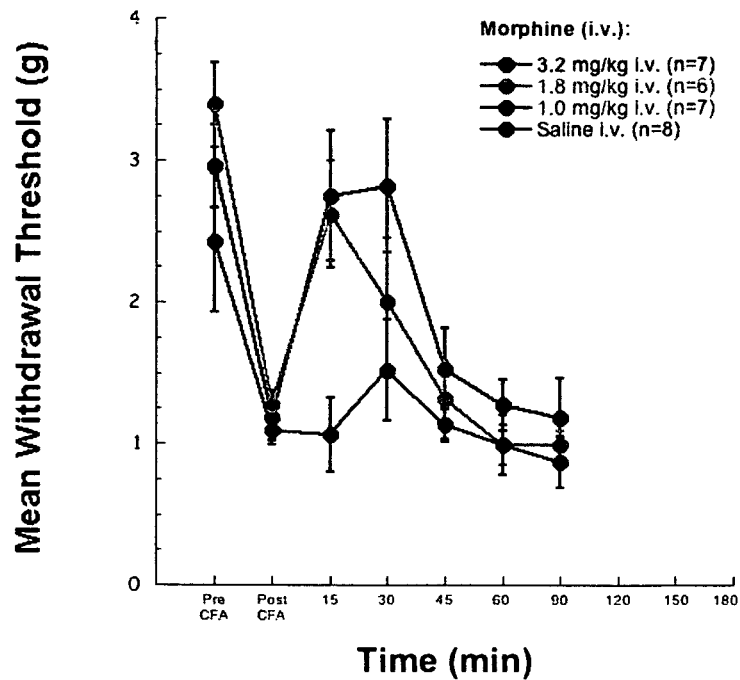
Figure 6b
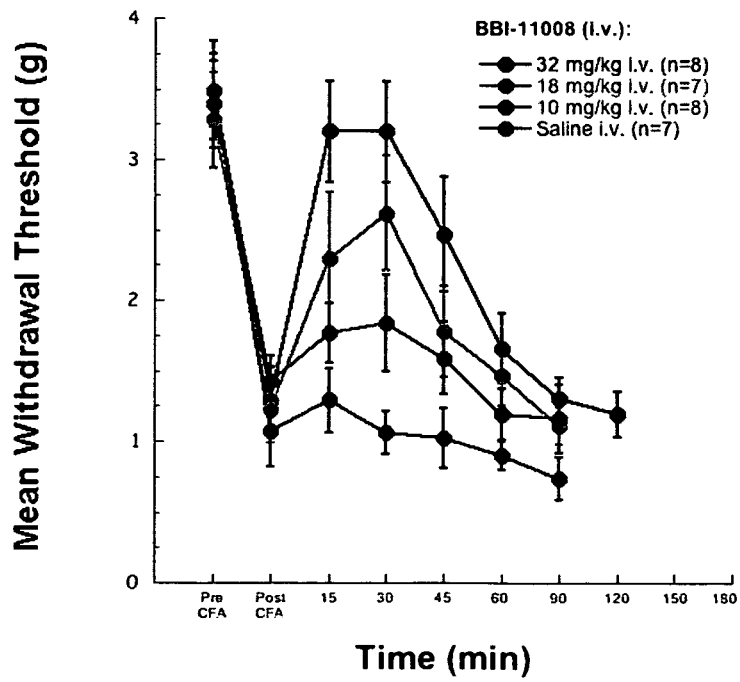

SEQUENCE LISTING

```
<160> NUMBER OF SEQ ID NOS: 29

<210> SEQ ID NO 1
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (2)..(2)
<223> OTHER INFORMATION: Xaa2 is selected from D-Alanine (dAla) and
      D-Methionine (dMet)
<220> FEATURE:
<221> NAME/KEY: Glycosylation
<222> LOCATION: (3)..(7)
<223> OTHER INFORMATION: At least one of Phe3, Xaa6 and Xaa7 are
      glycosylated
<220> FEATURE:
<221> NAME/KEY: MISC_FEATURE
<222> LOCATION: (4)..(4)
<223> OTHER INFORMATION: Xaa4 is selected from H, E, D and Q
<220> FEATURE:
<221> NAME/KEY: MISC_FEATURE
<222> LOCATION: (5)..(5)
<223> OTHER INFORMATION: Xaa5 is selected from L, V, I, C and Y
<220> FEATURE:
<221> NAME/KEY: MISC_FEATURE
<222> LOCATION: (6)..(6)
<223> OTHER INFORMATION: Xaa6 is selected from M, A, V, I, D, L, C, P
      and H
<220> FEATURE:
<221> NAME/KEY: MISC_FEATURE
<222> LOCATION: (7)..(7)
<223> OTHER INFORMATION: Xaa7 is selected from S, T, D, G, N, A and K

<400> SEQUENCE: 1

Tyr Xaa Phe Xaa Xaa Xaa Xaa
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: M = dMet
<220> FEATURE:
<221> NAME/KEY: Glycosylation
<222> LOCATION: (7)..(7)
<223> OTHER INFORMATION: Ser is glycosylated

<400> SEQUENCE: 2

Tyr Met Phe His Leu Met Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: Glycosylation
<222> LOCATION: (7)..(7)
<223> OTHER INFORMATION: Ser is glycosylated

<400> SEQUENCE: 3

Tyr Ala Phe His Leu Ala Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: M = dMet
<220> FEATURE:
<221> NAME/KEY: Glycosylation
<222> LOCATION: (7)..(7)
<223> OTHER INFORMATION: Thr is glycosylated

<400> SEQUENCE: 4

Tyr Met Phe His Leu Met Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: Glycosylation
<222> LOCATION: (7)..(7)
<223> OTHER INFORMATION: T is glycosylated

<400> SEQUENCE: 5
```

```
Tyr Ala Phe His Leu Ala Thr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: Met = dMet
<220> FEATURE:
<221> NAME/KEY: D-enantiomer
<222> LOCATION: (7)..(7)
<223> OTHER INFORMATION: Ser = dSer
<220> FEATURE:
<221> NAME/KEY: Glycosylation
<222> LOCATION: (7)..(7)
<223> OTHER INFORMATION: dSer is glycosylated

<400> SEQUENCE: 6

Tyr Met Phe His Leu Met Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: D-enantiomer
<222> LOCATION: (7)..(7)
<223> OTHER INFORMATION: S = dSer
<220> FEATURE:
<221> NAME/KEY: Glycosylation
<222> LOCATION: (7)..(7)
<223> OTHER INFORMATION: dSer is glycosylated

<400> SEQUENCE: 7

Tyr Ala Phe His Leu Ala Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (2)..(2)
<223> OTHER INFORMATION: Xaa2 is (dAla) or (dMet)
<220> FEATURE:
<221> NAME/KEY: MISC_FEATURE
<222> LOCATION: (3)..(3)
<223> OTHER INFORMATION: Xaa3 is F or A
<220> FEATURE:
<221> NAME/KEY: Glycosylation
<222> LOCATION: (3)..(7)
<223> OTHER INFORMATION: At least one of Xaa3, Xaa6 and Xaa7 are
      glycosylated
<220> FEATURE:
<221> NAME/KEY: MISC_FEATURE
<222> LOCATION: (4)..(4)
<223> OTHER INFORMATION: Xaa4 is H, E, D or Q
<220> FEATURE:
<221> NAME/KEY: MISC_FEATURE
<222> LOCATION: (5)..(5)
```

-continued

```
<223> OTHER INFORMATION: Xaa5 is Nva (Norvaline), Nle (Norleucine), L,
      V, I, C or Y
<220> FEATURE:
<221> NAME/KEY: MISC_FEATURE
<222> LOCATION: (6)..(6)
<223> OTHER INFORMATION: Xaa6 is Nva (Norvaline), Nle (Norleucine), L,
      V, I, M, A, D, C, P or H
<220> FEATURE:
<221> NAME/KEY: MISC_FEATURE
<222> LOCATION: (7)..(7)
<223> OTHER INFORMATION: Xaa7 is S, dSer, T, dThr, D, G, N, A or K

<400> SEQUENCE: 8

Tyr Xaa Xaa Xaa Xaa Xaa Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: MISC_FEATURE
<222> LOCATION: (5)..(6)
<223> OTHER INFORMATION: Xaa5 and Xaa6 are Nva (norvaline)
<220> FEATURE:
<221> NAME/KEY: Glycosylation
<222> LOCATION: (7)..(7)
<223> OTHER INFORMATION: S is glycosylated

<400> SEQUENCE: 9

Tyr Ala Phe Glu Xaa Xaa Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (norleucine)
<220> FEATURE:
<221> NAME/KEY: Glycosylation
<222> LOCATION: (7)..(7)
<223> OTHER INFORMATION: S is glycosylated

<400> SEQUENCE: 10

Tyr Ala Phe Glu Xaa Xaa Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: MISC_FEATURE
```

```
<222> LOCATION: (5)..(6)
<223> OTHER INFORMATION: Xaa5 and Xaa6 are Nva (Norvaline)
<220> FEATURE:
<221> NAME/KEY: Glycosylation
<222> LOCATION: (7)..(7)
<223> OTHER INFORMATION: T is glycosylated

<400> SEQUENCE: 11

Tyr Ala Phe Glu Xaa Xaa Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 12

Tyr Ala Phe His Xaa Xaa Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: MISC_FEATURE
<222> LOCATION: (5)..(6)
<223> OTHER INFORMATION: Xaa5 and Xaa6 are Nva (Norvaline)
<220> FEATURE:
<221> NAME/KEY: D-enantiomer
<222> LOCATION: (7)..(7)
<223> OTHER INFORMATION: S is dSer
<220> FEATURE:
<221> NAME/KEY: Glycosylation
<222> LOCATION: (7)..(7)
<223> OTHER INFORMATION: dSer is glycosylated

<400> SEQUENCE: 13

Tyr Ala Phe His Xaa Xaa Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A = dAla
<220> FEATURE:
<221> NAME/KEY: MISC_FEATURE
<222> LOCATION: (5)..(6)
```

```
<223> OTHER INFORMATION: Xaa5 and Xaa6 are Nle (Norleucine)
<220> FEATURE:
<221> NAME/KEY: D-enantiomer
<222> LOCATION: (7)..(7)
<223> OTHER INFORMATION: S = dSer
<220> FEATURE:
<221> NAME/KEY: Glycosylation
<222> LOCATION: (7)..(7)
<223> OTHER INFORMATION: dSer is glycosylated

<400> SEQUENCE: 14

Tyr Ala Phe His Xaa Xaa Ser
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (2)..(2)
<223> OTHER INFORMATION: Xaa2 is D-Alanine (dAla) or D-Methionine (dMet)
<220> FEATURE:
<221> NAME/KEY: Glycosylation
<222> LOCATION: (3)..(7)
<223> OTHER INFORMATION: At least one of Phe3, Xaa6 and Xaa7 is
      glycosylated
<220> FEATURE:
<221> NAME/KEY: MISC_FEATURE
<222> LOCATION: (4)..(4)
<223> OTHER INFORMATION: Xaa4 is H, E, D or Q
<220> FEATURE:
<221> NAME/KEY: MISC_FEATURE
<222> LOCATION: (5)..(5)
<223> OTHER INFORMATION: Xaa5 is L, V, Nva (Norvaline), Nle
      (Norleucine), I, C or Y
<220> FEATURE:
<221> NAME/KEY: MISC_FEATURE
<222> LOCATION: (6)..(6)
<223> OTHER INFORMATION: Xaa6 is L, V, Nva (Norvaline), Nle
      (Norleucine), I, M, A, D, L, C, P or H
<220> FEATURE:
<221> NAME/KEY: MISC_FEATURE
<222> LOCATION: (7)..(7)
<223> OTHER INFORMATION: Xaa7 is S, D-Serine (dSer), T,  D-Threonine
      (dThr), D, G, N, A or K
<220> FEATURE:
<221> NAME/KEY: MISC_FEATURE
<222> LOCATION: (8)..(12)
<223> OTHER INFORMATION: Each of Xaa8 through Xaa12 is either absent or
      is any amino acid

<400> SEQUENCE: 15

Tyr Xaa Phe Xaa Xaa Xaa Xaa Xaa Xaa Xaa Xaa Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (1)..(1)
<223> OTHER INFORMATION: Xaa1 is selected from Y, Dmt
      (2,5-dimethyltyrosine) and Tmt (2,5,beta-trimethyltyrosine (R,S
      isomer))
<220> FEATURE:
<221> NAME/KEY: MISC_FEATURE
<222> LOCATION: (2)..(2)
<223> OTHER INFORMATION: Xaa2 is selected from D-Alanine (dAla),
      D-Methionine (dMet), and D-valine (dVal), and
      alpha-aminoisobutyric acid
```

```
<220> FEATURE:
<221> NAME/KEY: MISC_FEATURE
<222> LOCATION: (3)..(3)
<223> OTHER INFORMATION: Xaa3 is selected from F, Tic
      (tetrahydroisoquinoline-3-carboxylic
      acid) and Nmf (N-methylphenylalanine)
<220> FEATURE:
<221> NAME/KEY: Glycosylation
<222> LOCATION: (3)..(7)
<223> OTHER INFORMATION: At least one of Xaa3, Xaa6 and Xaa7 is
      glycosylated
<220> FEATURE:
<221> NAME/KEY: MISC_FEATURE
<222> LOCATION: (4)..(4)
<223> OTHER INFORMATION: Xaa4 is selected from H, E, D, Q and F
<220> FEATURE:
<221> NAME/KEY: MISC_FEATURE
<222> LOCATION: (5)..(5)
<223> OTHER INFORMATION: Xaa5 is selected from L, V, I, C, Y, A, Nva
      (Norvaline) and Nle (Norleucine)
<220> FEATURE:
<221> NAME/KEY: MISC_FEATURE
<222> LOCATION: (6)..(6)
<223> OTHER INFORMATION: Xaa6 is selected from M, V, I, D, L, C, P, H,
      A, T, Nva (Norvaline) and Nle (Norleucine)
<220> FEATURE:
<221> NAME/KEY: MISC_FEATURE
<222> LOCATION: (7)..(7)
<223> OTHER INFORMATION: Xaa7 is selected from D, G, N, S, A, K, T,
      D-Serine (dSer), and D-Threonine (dThr)
<220> FEATURE:
<221> NAME/KEY: MISC_FEATURE
<222> LOCATION: (8)..(12)
<223> OTHER INFORMATION: Each of Xaa8 through Xaa12 is either absent or
      is any amino acid

<400> SEQUENCE: 16

Xaa Xaa Xaa Xaa Xaa Xaa Xaa Xaa Xaa Xaa Xaa Xaa
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: D-enantiomer
<222> LOCATION: (7)..(7)
<223> OTHER INFORMATION: T is dThr
<220> FEATURE:
<221> NAME/KEY: Glycosylation
<222> LOCATION: (7)..(7)
<223> OTHER INFORMATION: dThr is glycosylated

<400> SEQUENCE: 17

Tyr Ala Phe Glu Xaa Xaa Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
```

```
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: D-enantiomer
<222> LOCATION: (7)..(7)
<223> OTHER INFORMATION: S is dSer
<220> FEATURE:
<221> NAME/KEY: Glycosylation
<222> LOCATION: (7)..(7)
<223> OTHER INFORMATION: dSer is glycosylated

<400> SEQUENCE: 18

Tyr Ala Phe Glu Xaa Xaa Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 or Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 19

Tyr Ala Phe Glu Xaa Xaa Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 20

Tyr Ala Phe Glu Xaa Xaa Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
```

-continued

```
<220> FEATURE:
<221> NAME/KEY: Glycosylation
<222> LOCATION: (7)..(7)
<223> OTHER INFORMATION: T is glycosylated

<400> SEQUENCE: 21

Tyr Ala Phe Glu Ile Ile Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: Glycosylation
<222> LOCATION: (7)..(7)
<223> OTHER INFORMATION: S is glycosylated

<400> SEQUENCE: 22

Tyr Ala Phe Glu Val Val Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (1)..(1)
<223> OTHER INFORMATION: X1 is Dmt (2,5-dimethyltyrosine)
<220> FEATURE:
<221> NAME/KEY: D-entantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 23

Xaa Ala Phe Glu Xaa Xaa Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (3)..(3)
<223> OTHER INFORMATION: Xaa3 is Tic
      (tetrahydroisoquinoline-3-carboxylic acid)
<220> FEATURE:
<221> NAME/KEY: MISC_FEATURE
<222> LOCATION: (5)..(6)
<223> OTHER INFORMATION: Xaa5 and Xaa6 are Nle (Norleucine)
```

```
<220> FEATURE:
<221> NAME/KEY: Glycosylation
<222> LOCATION: (7)..(7)
<223> OTHER INFORMATION: T is glycosylated

<400> SEQUENCE: 24

Tyr Ala Xaa Glu Xaa Xaa Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (2)..(2)
<223> OTHER INFORMATION: Xaa2 is alpha-aminoisobutyric acid
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 25

Tyr Xaa Phe Glu Xaa Xaa Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: MISC_FEATURE
<222> LOCATION: (1)..(1)
<223> OTHER INFORMATION: Xaa1 is Tmt (2,5,beta-trimethyltyrosine (R,S
    isomer))
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 26

Xaa Ala Phe Glu Xaa Xaa Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (3)..(3)
<223> OTHER INFORMATION: Xaa3 is Nmf (N-methylphenylalanine)
```

```
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: T is glycosylated

<400> SEQUENCE: 27

Tyr Ala Xaa Glu Xaa Xaa Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: MISC_FEATURE
<222> LOCATION: (5)..(6)
<223> OTHER INFORMATION: Xaa5 and Xaa6 are Nle (Norleucine)
<220> FEATURE:
<221> NAME/KEY: Glycosylation
<222> LOCATION: (7)..(7)
<223> OTHER INFORMATION: S is glycosylated

<400> SEQUENCE: 28

Tyr Ala Phe Glu Xaa Xaa Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic glycopeptide
<220> FEATURE:
<221> NAME/KEY: D-enantiomer
<222> LOCATION: (2)..(2)
<223> OTHER INFORMATION: A is dAla
<220> FEATURE:
<221> NAME/KEY: Glycosylation
<222> LOCATION: (7)..(7)
<223> OTHER INFORMATION: S is glycosylated

<400> SEQUENCE: 29

Tyr Ala Phe Glu Val Val Ser
1               5
```

DELTA-OPIOID RECEPTOR SELECTIVE ANALGESICS

RELATED APPLICATIONS

This application is a continuation-in-part of provisional patent application, Ser. No. 61/201,159, filed on Dec. 8, 2008; and provisional patent application, Ser. No. 61/277,279, filed on Sep. 23, 2009. The disclosure of both of these documents is hereby incorporated herein by reference.

This application includes as part of its subject matter a substitute Sequence Listing electronically submitted via EFS-Web on May 20, 2013, as a single text file named "SUBSTITUTE_SEQUENCE_LISTING_ST25.txt". The substitute Sequence Listing text file was created on May 20, 2013 and is 16 kb in size. The contents of the substitute Sequence Listing are hereby incorporated by reference.

FIELD OF THE INVENTION

The present invention relates to glycosylated peptides with high affinity for the delta opioid receptors. The peptides, and compositions comprising them, are useful for treatment of pain, including nociceptive, inflammatory, neuropathic and bone and osteoporosis pain.

BACKGROUND OF THE INVENTION

Throughout the history of human medicine, various compounds have been used for the relief of pain. In particular, a class of compounds of plant origin known as opiates has been used since prehistoric periods for analgesic and euphoric purposes. Even today the opiate drug morphine is used as an analgesic for significant pain, and morphine is still an important benchmark for clinical studies: Morphine is the most widely prescribed injectable opioid today, despite its narcotic side effects. The opioid derivative hydrocodone is the most commonly prescribed drug in the United States. Acute opioid toxicity from overdose can result in respiratory depression and death, whereas chronic use can lead to physical dependence, addiction, and severe opioid-induced bowel dysfunction.

Despite significant side effects, opioids are the first choice for the treatment of moderate to severe pain (including inflammatory), both acute and chronic. Current analgesics, including morphine, fentanyl, oxycodone and hydrocodone act primarily at mu-opioid receptors (MOR). Activation of this receptor subtype is responsible for many of the side effects associated with these drugs, such as respiratory depression, constipation, addiction, dependence, and immunosuppression. These side effects limit the use of morphine and other opioids to treat both acute and chronic pain.

Currently available opioid drugs are the primary choice for the treatment of moderate to severe pain and account for over 180 million prescriptions annually in the United States. Representative opioid drugs in this list include hydrocodone, oxycodone, oxymorphone, codeine, methadone and morphine.

The majority of clinically available opioids act almost exclusively at the MOR. Agonism of the MOR mediates not only the analgesic actions of this class of drugs, but also many of the side effects of opioids including respiratory depression, constipation, addiction liability, tolerance/physical dependence and immunosuppression. These side effects significantly limit the usefulness of opioid analgesics, especially in cases of non-malignant chronic pain. An additional constraint in the reliance upon MOR selective analgesics is their limited efficacy in certain inflammatory and neuropathic pain states, requiring dose escalations that further increase compound side effects. These shortcomings drive the sustained efforts to develop novel analgesics that have equivalent or better efficacy compared to conventional opioids for a variety of pain states, while limiting the side effect potential.

Endogenous opioid peptides synthesized by vertebrates in general, and mammals in particular, bind to the same receptors as the exogenous opioid molecules including morphine. The endogenous peptides are known by the generic terms endorphins, and endorphins have been subject of much discussion and research since their discovery in the 1970s. These endogenous opioids are believed to be the natural source of various euphoric experiences reported by people, including the "runner's high" and the feelings experienced by some after eating chocolate. Although the evidence about these experiences is to a large degree subjective, there is no question that endogenous opioid peptides play a critical role in the various sensory emotional motivational and cognitive functions.

A related class of endogenous opioids has been isolated from amphibian skin extracts and are known as the deltorphins. Deltorphins are small peptides that display high specificity. There are both natural and synthetic deltorphins. Deltorphins are well known to actively engage the opioid receptors and can produce strong analgesic effects when delivered to the brain or spinal cord. However, the use of endorphins in general, and deltorphins in particular, has not moved from the theoretical to the therapeutic reality, in large part based on difficulties in their administration and stability, and an inability to deliver the molecules across the blood brain barrier.

Delta Opioid Receptors (DOR) were first described in 1977 (Lord et al., 1977) and subsequently, several classes of peptide and non-peptide based molecules have been synthesized that selectively stimulate this receptor. Selective DOR molecules include the modified enkephalin analog, DPDPE (Mosberg et al., 1983), deltorphin-based peptides (Kreil et al., 1989) and analogs of BW373U86 (e.g., SNC80; Bilsky et al., 1994; Calderon et al., 1994; 2004). Preclinical efficacy studies of these compounds, along with DOR-selective antagonists, provide a convincing rationale for pursuing DOR agonists as analgesic agents. In addition, DOR knockout mice exhibit increased pain behaviors following an inflammatory or neuropathic-based insult (Gavériaux-Ruff et al., 2008; Nadal et al., 2006). Interestingly, upregulation and altered trafficking of DOR occurs following induction of various pain states in rodents (Cahill et al., 2003; 2007; Walwyn et al., 2005). DOR selective compounds also have significantly reduced the tumor burden in multiple animal models.

There is a critical need for improved opioids with high efficacy, but without the severe side effects associated with currently available therapies. Accordingly, the present invention addresses this need by using novel synthetic chemistry to generate novel compounds that have improved pharmacological properties for targeting DOR.

BRIEF SUMMARY OF THE INVENTION

The present invention provides novel peptides with high affinity for the delta opioid receptor (DOR), and methods for preparing and using these peptides for the treatment of conditions that involve pain, such as acute and chronic pain including inflammatory and neuropathic pain states. The invention also provides methods for delivering analgesia or relief from pain to an individual by administering to the bloodstream an effective amount of an analgesic molecule, which is a glycosylated peptide. In certain aspects, the invention comprises method of treatment of pain due to cancer. The invention also provides methods for the treatment and prevention or amelioration of neurological conditions, such as Parkinson's Disease, Alzheimer's Disease, Pick's Disease, and Chronic Fatigue Syndrome, and treatment of emotional or mood disorders. In certain embodiments, the glycosylated peptides of the present invention comprise glycosylated variants of deltorphins, or closely related peptides. The glycosylated peptides of the present invention are typically between six and twelve amino acids in length, more preferably between seven and ten amino acids in length. In certain embodiments, the peptide is glycosylated with a sugar moiety selected from a monosaccharide, disaccharide or trisaccharide sugar moiety. In certain embodiments, the peptides have low affinity for one or more opioid receptors other than the DOR, such as the kappa opioid receptor (KOR) or the mu opioid receptor (MOR), or both.

In other embodiments, the glycosylated peptides of the present invention are formulated into compositions, which compositions may be used for the treatment of neurological conditions, including conditions that involve pain, such as acute and chronic pain including inflammatory and neuropathic pain states. The compositions may include one or more additional active agents, such as anti-inflammatory agents or anti-pain agents, as well as one or more inactive agents, which may include carriers, delivery vehicles, binding agents, diluents, disintegrants, lubricants, buffers, and other pharmaceutically acceptable excipients.

In specific embodiments, the present invention includes glycosylated peptides comprising the following amino acid sequence:

[SEQ ID NO: 1]
X1-X2-X3-X4-X5-X6-X7-W wherein:
W is selected from NH2 and OH;
X1 is Y;
X2 is selected from D-Alanine (dAla) and D-Methionine (dMet);
X3 is F;
X4 is selected from H, E, D and Q;
X5 is selected from L, V, I, C and Y;
X6 is selected from M, A, V, I, D, L, C, P and H;
X7 is selected from S, T, D, G, N, A and K;
and wherein at least one of X3, X6 and X7 is glycosylated. In preferred embodiments, at least one of X3, X6 and X7 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

In other embodiments, the glycosylated peptide of the present invention comprises an amino acid sequence selected from the group consisting of:

[SEQ ID NO: 2]
Y-dMet-F-H-L-M-Ser(beta-D-Glc)W;

[SEQ ID NO: 3]
Y-dAla-F-H-L-A-Ser(beta-D-Glc)W;

[SEQ ID NO: 4]
Y-dMet-F-H-L-M-Thr(beta-D-Glc)W;

[SEQ ID NO: 5]
Y-dAla-F-H-L-A-Thr(beta-D-Glc)W;

[SEQ ID NO: 6]
Y-dMet-F-H-L-M-dSer(beta-D-Glc)W;
and

[SEQ ID NO: 7]
Y-dAla-F-H-L-A-dSer(beta-D-Glc)W, wherein W is selected from NH2 and OH and Glc is glucose.

In other embodiments, the glycosylated peptide of the present invention comprises the following amino acid sequence:

[SEQ ID NO: 8]
X1-X2-X3-X4-X5-X6-X7-W wherein:
W is selected from NH2 and OH;
X1 is Y;
X2 is selected from D-Alanine (dAla) and D-Methionine (dMet);
X3 is selected from F and A;
X4 is selected from H, E, D and Q;
X5 is selected from Nva, Nle, L, V, I, C and Y;
X6 is selected from Nva, Nle, L, V, I, M, A, D, C, P and H;
X7 is selected from S, dSer, T, dThr, D, G, N, A and K;
and wherein at least one of X3, X6 and X7 is glycosylated. In preferred embodiments, at least one of X3, X6 and X7 is glycosylated with a sugar residue selected from the group consisting of glucose; galactose; xylose; fructose; mannose; fucose; ribose; deoxyribose; arabinose; rhamnose; sucrose; trehalose; saccharose; maltose; and lactose.

Certain preferred glycosylated peptides of the present invention include glycosylated peptides comprising an amino acid sequence selected from the group consisting of:

[SEQ ID NO: 9]
Y-dAla-F-E-Nva-Nva-Ser(beta-D-Glc)W;

[SEQ ID NO: 10]
Y-dAla-F-E-Nle-Nle-Ser(beta-D-Glc)W;

[SEQ ID NO: 11]
Y-dAla-F-E-Nva-Nva-Thr(beta-D-Glc)W;

[SEQ ID NO: 12]
Y-dAla-F-H-Nle-Nle-Thr(beta-D-Glc)W;

[SEQ ID NO: 13]
Y-dAla-F-H-Nva-Nva-dSer(beta-D-Glc)W;
and

[SEQ ID NO: 14]
Y-dAla-F-H-Nle-Nle-dSer(beta-D-Glc)W, wherein W is selected from NH2 and OH; and Glc is glucose.

Additional glycosylated peptides of the present invention comprise the following amino acid sequence:

[SEQ ID NO: 15]
X1-X2-X3-X4-X5-X6-X7-Z-W wherein: X1 is Y;
X2 is selected from D-Alanine (dAla) and D-Methionine (dMet);
X3 is F;
X4 is selected from H, E, D and Q;
X5 is selected from L, V, Nva, Nle, I, C and Y;
X6 is selected from L, V, Nva, Nle, I, M, A, D, L, C, P and H;

X7 is selected from S, D-Serine (dSer), T, D-Threonine (dThr), D, G, N, A and K;

W is selected from NH2 and OH;

Z is selected from a sequence of 0 to 5 amino acids.

and wherein at least one of X3, X6 and X7 is glycosylated. In preferred embodiments, at least one of X3, X6 and X7 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

In other preferred embodiments of the present invention, the glycosylated peptide comprises the following amino acid sequence:

[SEQ ID NO: 16]
X1-X2-X3-X4-X5-X6-X7-Z-W wherein:

X1 is selected from Y; Dmt and Tmt;

X2 is selected from D-Alanine (dAla), D-Methionine (dMet), and D-valine (dVal); and B;

X3 is selected from F; Tic and Nmf;

X4 is selected from H, E, D; Q and F;

X5 is selected from L, V, I, C, Y, A, Nva and Nle;

X6 is selected from M, V, I, D, L, C, P, H, A, T, Nva and Nle;

X7 is selected from D, G, N, S, A, K, T, D-Serine (dSer), and D-Threonine (dThr);

W is selected from NH2 and OH;

Z is selected from a' sequence of 0 to 5 amino acids, wherein at least one of X3, X6 and X7 is glycosylated, each of A, C, D, F, G, H, I, K, L, M, N, P, Q, S, T, V and Y are understood to represent commonly known amino acids, and wherein:

Dmt=2,5-dimethyltyrosine

Tic=tetrahydroisoquinoline-3-carboxylic acid

B=alpha-aminoisobutyric acid

Tmt=2,5,beta-trimethyltyrosine (R,S isomer)

Nmf=N-methylphenylalanine

Nva=L-norvaline

Nle=L-norleucine.

In preferred embodiments, at least one of X3, X6 and X7 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

Specific preferred glycosylated peptides of the invention comprise an amino acid sequence selected from the group consisting of:

[SEQ ID NO: 17]
Y-dAla-F-E-Nle-Nle-dThr(beta-D-Glc)NH2;

[SEQ ID NO: 18]
Y-dAla-F-E-Nle-Nle-dSer(beta-D-Glc)NH2;

[SEQ ID NO: 19]
Y-dAla-F-E-Nle-Nle-Thr(beta-D-Rhamnoside)NH2;

[SEQ ID NO: 20]
Y-dAla-F-E-Nle-Nle-Thr(beta-Lactoside)NH2;

[SEQ ID NO: 21]
Y-dAla-F-E-I-I-Thr(beta-D-Glc)NH2;

[SEQ ID NO: 22]
Y-dAla-F-E-V-V-Ser(beta-D-Glc)NH2;

-continued

[SEQ ID NO: 23]
Dmt-dAla-F-E-Nle-Nle-Thr(beta-D-Glc)NH2;

[SEQ ID NO: 24]
Y-dAla-Tic-E-Nle-Nle-Thr(beta-D-Glc)NH2;

[SEQ ID NO: 25]
Y-B-F-E-Nle-Nle-Thr(beta-D-Glc)NH2;

[SEQ ID NO: 26]
Tmt-dAla-F-E-Nle-Nle-Thr(beta-D-Glc)NH2;

[SEQ ID NO: 27]
Y-dAla-Nmf-E-Nle-Nle-Thr(beta-D-Glc)NH2;

[SEQ ID NO: 28]
Y-dAla-F-E-Nle-Nle-Ser(beta-D-Lactoside)NH2;
and

[SEQ ID NO: 29]
Y-dAla-F-E-V-V-Ser(beta-Lactoside)NH2;

In certain embodiments, the glycosylated peptide of the present invention comprises one or more glycosylated residues, preferably from 1 to 3 amino acids to which a glycan moiety has been attached. The glycan moiety is preferably a saccharide, including mono-, di- and trisaccharides. In other embodiments, the glycan moiety may be an oligosaccharide [with four or more linked saccharide] or a polysaccharide. Other molecules, such as glycosaminoglycans may also be used as one or more glycan moiety attached to the peptide chains. The glycans may be attached to the peptide through any known means, whether enzymatic or synthetic, including means described in U.S. Pat. Nos. 5,470,949 and 5,767,254, the disclosure of which are hereby incorporated by reference.

In preferred embodiments, at least one of X3, X6 and X7 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

Other object advantages and features of the present invention will be apparent from the following specification.

BRIEF DESCRIPTION OF THE FIGURES

FIG. 4 illustrates the peptide and glycoside structures of glycopeptides 11001 through 11020.

FIG. 5 illustrates the results of a CFA Inflammatory Pain Assay measuring thermal sensitivity. FIG. 5a illustrates the results with various doses of morphine in saline vehicle. FIG. 5b illustrates the results with various doses of glycopeptide 11008 in saline vehicle.

FIG. 6 illustrates the results of a CFA Inflammatory Pain Assay measuring tactile sensitivity. FIG. 6a illustrates the results with various doses of morphine in saline vehicle. FIG. 6b illustrates the results with various doses of glycopeptide 11008 in saline vehicle.

DETAILED DESCRIPTION OF THE INVENTION

Figure 1:
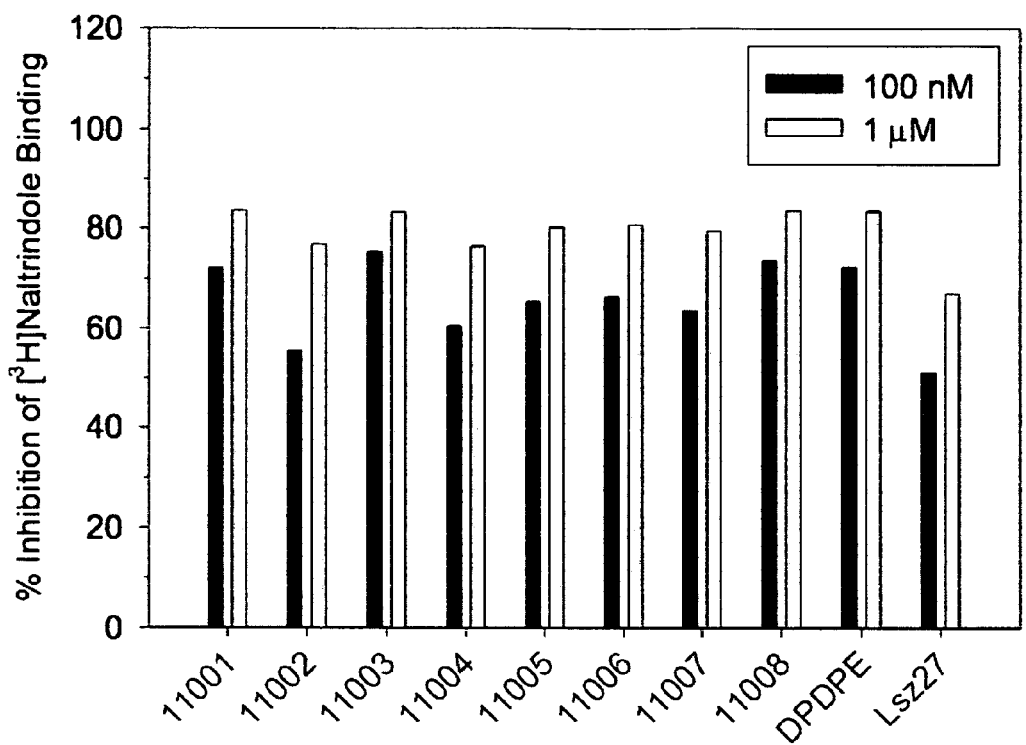
FIG. 1 illustrates the % inhibition of tritium-labeled Naltrinidole binding by glycopeptides 11001 through 11008, compared with DPDPE and Lsz27.

The present invention provides novel DOR-selective compounds, as well as methods for their preparation, screening and use for the treatment of various physical and physiological ailments. The novel glycopeptides comprise a basic deltorphin scaffold, with variations in certain amino acid residues, as well as variations of saccharide moieties attached at certain amino acid residues.

Glycopeptides are synthesized and screened for in vitro binding, selectivity and activity at opioid receptors. High affinity (Ki<10 nM), DOR-selective compounds are identified and tested in vivo in an acute pain model and further tested in a sub-acute inflammatory pain model, both of which are sensitive to DOR agonists. These compounds will be tested upon multiple models of analgesia, including the treatment of chronic inflammatory pain.

The ability to synthesize glycosylated peptides is utilized to develop deltorphin-based peptides to develop novel, safe and efficacious targeted delivery of compounds for the treatment of pain and other diseases (e.g.: cancer, and inflammation). Glycosylation of the deltorphin scaffold will enhance the efficacy of this family of DOR agonists. Current data indicate that these compounds are particularly efficacious in chronic inflammatory and neuropathic pain states. This invention further comprises methods for synthesizing a library of deltorphin-based glycopeptides and obtain dosing and efficacy data in preclinical rodent models of acute and sub-acute pain.

It is expected that the effective doses will not be associated with traditional MOR-mediated side effects. In the unlikely event that intolerable side effects are present, then that information will be used to help guide further refinement of the synthesis of deltorphin-based glycopeptides, or alternatively, another DOR-selective scaffold. In the event that minimal activity is observed in the assay, an alternative acute/sub-acute antinociceptive assay will be employed (e.g., carrageenan) to assess potency and efficacy. The milestone will consist of the identification of a compound with antinociceptive activity and no significant gross observable side effects.

The abuse potential and physical dependence liability of opioid analgesics is another important area in which compounds that act at both DOR and MOR may have significant advantages.

DOR-selective agonists display potent and fully effective antinociception in a variety of pain models and different species, and many groups have pursued the DOR as a target for the treatment of chronic pain (Aceto et al., 2007; Dolle et al., 2007). Fraser and colleagues demonstrated that deltorphin II and SNC80 both produced dose-related reversal of hyperalgesia associated with CFA-induced paw inflammation (Fraser et al., 2000). DOR agonists have also produced efficacy in neuropathic and bone cancer models of pain (Brainin-Mattos et al., 2006; Holdridge & Cahill, 2007; Mika et al., 2001). ADL5859, a selective DOR agonist currently in clinical trials, was shown to be active in preclinical inflammatory and neuropathic pain models (Adolor Corp. website: www.adolor.com).

In addition to providing analgesia, DOR agonists display fewer side effects than equivalent doses of traditional MOR agonists. Cheng and colleagues (1993) demonstrated that a deltorphin-based peptide could stimulate (rather than depress) respiration in a fetal sheep model. Extending this finding, DOR agonists were shown to reverse MOR agonist-induced respiratory depression in rats without decreasing alfentanil antinociception (Su et al., 1998). In a comparison study of morphine and SNC80, Gallantine and Meert (2005) concluded that SNC80 did not induce muscle rigidity, or block pinna and cornea reflexes, indicating the lack of MOR-mediated effects. SNC80 produced less pronounced effects on GI transit and there was also a larger separation between rotorod performance impairment and antinociception with SNC80 compared to morphine, a result that is consistent with findings using DPDPE (Franck et al., 1991).

Interestingly, DOR agonists have also been reported to reverse MOR agonist-induced rigidity (Vankova et al. 1996), a side effect that contributes to respiratory depression. In rhesus monkeys, SNC80 did not support self-administration indicating low abuse potential for the compound (Stevenson et al., 2005). There is also evidence that DOR agonists have antidepressant properties (Jutkiewicz, 2006; Torregrossa et al., 2006), a highly desirable effect given the high incidence of depression in chronic pain patients.

Collectively, the preclinical pharmacology of DOR agonists supports targeted drug development efforts and several pharmaceutical companies have active programs in place. The most advanced DOR selective agonist, ADL5859 (Adolor Corp.), is currently in Phase IIa clinical trials for pain associated with rheumatoid arthritis, osteoarthritis and diabetic peripheral neuropathy. Phase I studies indicated that the compound was orally bioavailable and well-tolerated in humans. In November 2007, Adolor announced an exclusive, world-wide collaboration with Pfizer, Inc. to develop and commercialize their DOR compounds, including ADL5859 (see: www.adolor.com).

Targeted Glycosylation of Opioid Peptides. Glycosylation of proteins has significant effects on the stability and activity of protein therapeutics (Solá et al., 2007). The inventors and others have shown that glycosylation is a viable strategy for improving stability and tissue-targeted delivery of peptides (Polt et al., 1994, 2005; Susaki et al., 1999). The inventors' work initially focused on endogenous enkephalins (leucine and methionine) due to their potent analgesic effects, roughly equal affinity for DOR and MOR, and clinical studies demonstrating analgesic efficacy in morphine-tolerant cancer patients (Onofrio & Yaksh, 1983; Moulin et al., 1985). Although poor PK limited further development of the native enkephalin peptides, and initial research confirmed the hypothesis that glycosylation of this scaffold could improve stability and CNS bioavailability in preclinical models.

The opioid receptors are all GPCRs and have been effectively modeled using X-ray coordinates of other GPCRs, followed by in silico replacement of individual amino acids to obtain an accurate representation of the receptors for use in docking calculations (receptor homology modeling). This approach has been used to choose the peptide sequences and optimal sites for glycosylation and is an important component in the CarboSyn™ process. Most of the starting opioid peptide sequences have been validated by in vitro binding studies of enkephalin, deltorphin, dynorphin and endorphin peptides (Strange, 2008). Deltorphin C (deltorphin II) belongs to a family of heptapeptides isolated from skin extracts of frogs belonging to the genus *Phyllomedusa*. BBI has expanded its validated peptide modification algorithm and is using it to build a new library derived from the deltorphin family of peptides. Deltorphins have an almost thousand fold increase in binding preference for human DOR vs. MOR (Tancredi et al., 1991; Tomatis et al., 1997). However, limited ability of the native deltorphin peptide to cross the blood-brain barrier has prevented advancement to the clinic.

Initial studies of a deltorphin peptide modified through glycosylation at the seventh residue indicated increased antinociceptive potency (4 fold greater than the initial peptide) when administered subcutaneously (sc). These data provide additional validation of glycosylation as a tool to increase the PK and efficacy of native peptides. Additional studies are planned to confirm the hypothesis that specific sugars enhance CNS delivery (and targeted CNS exclusion) of synthetic, modified glycopeptides.

The endogenous peptide family, deltorphins, is proven to be highly delta-opioid receptor (DOR) selective. It is hypothesized that increasing the DOR selectivity of glycopeptides further enhances antinociceptive efficacy, while reducing or avoiding the side effects typically seen with MOR-selective analgesics. Thus, the novel class of compounds produced herein represent a promising new class of drugs for use in addressing the unmet needs in chronic pain, namely improved efficacy and reduced side effect liability with long-term dosing.

TABLE 1

DELTORPHIN PEPTIDE SEQUENCES

|  | 1 | 2 [dX] | 3* | 4 | 5 | 6* | 7* |
|---|---|---|---|---|---|---|---|
| Deltorphin A | Y | dMet | F | H | L | M | Asp-NH2 |
| Deltorphin B | Y | dA | F | E | V | V | Gly-NH2 |
| Deltorphin C | Y | dA | F | D | V | V | Gly-NH2 |

The present invention includes the synthesis and purification of the novel deltorphin-related glycopeptides described in Tables 2, 3 and 4:

TABLE 2

NOVEL VARIANT/GLYCOSYLATED
DELTORPHINS PEPTIDE SEQUENCES

|  | 1 | 2 | 3* | 4 | 5 | 6* | 7* |
|---|---|---|---|---|---|---|---|
| CONSENSUS | Y | dA | F | H | L | M | D-NH2 |
|  |  | dM |  | E | V | V | G-NH2 |
|  |  | dV |  | D | I | I | N-NH2 |
|  |  |  |  | Q | C | D | S-NH2 |
|  |  |  |  | F | Y | L | A-NH2 |
|  |  |  |  |  | A | C | K-NH2 |
|  |  |  |  |  | Nva | P |  |
|  |  |  |  |  | Nle | H |  |
|  |  |  |  |  |  | A |  |
|  |  |  |  |  |  | T |  |
|  |  |  |  |  |  | Nva |  |
|  |  |  |  |  |  | Nle |  |

*-Site for potential glycosylation

TABLE 3

NOVEL VARIANT/GLYCOSYLATED
DELTORPHIN A PEPTIDE SEQUENCES

| Deltorphin A | 1 | 2 [dX] | 3 4 5 6 7 |
|---|---|---|---|
| Deltorphin A1 | Y | dMet | F H L M Ser(beta-D-Glc)-NH2 |
| Deltorphin A2 | Y | dAla | F H L A Ser(beta-D-Glc)-NH2 |
| Deltorphin A3 | Y | dMet | F H L M Thr(beta-D-Glc)-NH2 |
| Deltorphin A4 | Y | dAla | F H L A Thr(beta-D-Glc)-NH2 |
| Deltorphin A5 | Y | dMet | F H L M dSer(beta-D-Glc)-NH2 |
| Deltorphin A6 | Y | dAla | F H L A dSer(beta-D-Glc)-NH2 |

TABLE 4

NOVEL VARIANT/GLYCOSYLATED
DELTORPHIN B PEPTIDE SEQUENCES

| Deltorphin B | 1 | 2 [dX] | 3 4 5 6 7 |
|---|---|---|---|
| Deltorphin B1 | Y | dAla | F E Nva Nva Ser(beta-D-Glc)-NH2 |
| Deltorphin B2 | Y | dAla | F E Nle Nle Ser(beta-D-Glc)-NH2 |
| Deltorphin B3 | Y | dAla | F E Nva Nva Thr(beta-D-Glc)-NH2 |
| Deltorphin B4 | Y | dAla | F E Nle Nle Thr(beta-D-Glc)-NH2 |
| Deltorphin B5 | Y | dAla | F E Nva Nva dSer(beta-D-Glc)-NH2 |
| Deltorphin B6 | Y | dAla | F E Nle Nle dSer(beta-D-Glc)-NH2 |

Additional Compounds.

Based upon initial testing, the inventors designed additional glycosylated variants of opioid receptors which follow the consensus sequence described in Table 5 below.

TABLE 5

ADDITIONAL NOVEL VARIANT/GLYCOSYLATED
DELTORPHINS PEPTIDE SEQUENCES

|  | 1 | 2 | 3* | 4 | 5 | 6* | 7* | 8* | 9 |
|---|---|---|---|---|---|---|---|---|---|
| CONSENSUS | Y | dA | F | H | L | M | D | S | G |
|  | Dmt | dM | Tic | E | V | V | G | -NH2 |  |
|  | Tmt | dV | Nmf | D | I | I | N |  |  |
|  |  | B |  | Q | C | D | S |  |  |
|  |  |  |  | F | Y | L | A |  |  |
|  |  |  |  |  | A | C | K |  |  |
|  |  |  |  |  | Nva | P | T |  |  |
|  |  |  |  |  | Nle | H | dT |  |  |
|  |  |  |  |  |  | A | dS |  |  |
|  |  |  |  |  |  | T | -NH2 |  |  |
|  |  |  |  |  |  | Nva |  |  |  |
|  |  |  |  |  |  | Nle |  |  |  |

*-Site for potential glycosylation
Dmt = 2,5-dimethyltyrosine
Tic = tetrahydroisoquinoline-3-carboxylic acid
B = alpha-aminoisobutyric acid
Tmt = 2,5,beta-trimethyltyrosine (R,S isomer)
Nmf = N-methylphenylalanine
Nva = L-norvaline
Nle = L-norleucine The design of additional compounds includes testing compounds with sugar residues with increased lipophilicity or hydrophilicity, as well as other parameters, such as amphipathicity (Lowery et al. 2007) designed to decrease Ki delta and/or increase the ratio of Ki mu:Ki delta. Additional compounds according to the present invention include those listed in FIG. 4 and summarized below in Table 6 below:

TABLE 6

SEQUENCE OF ADDITIONAL GLYCOPEPTIDES

| PEPTIDE | SEQUENCE |
|---|---|
| BBI-11009 | $H_2N$-YaFE-Nle-Nle-T-amide (Control) |
| BBI-11010 | $H_2N$-YaFE-Nle-Nle-t(beta-D-Glc)-amide |
| BBI-11011 | $H_2N$-YaFE-Nle-Nle-s(beta-D-Glc)-amide |
| BBI-11012 | $H_2N$-YaFE-Nle-Nle-T(beta-D-Rhamnoside)-amide |
| BBI-11013 | $H_2N$-YaFE-Nle-Nle-T(beta-Lactoside)-amide |

TABLE 6-continued

SEQUENCE OF ADDITIONAL GLYCOPEPTIDES

| PEPTIDE | SEQUENCE |
|---|---|
| BBI-11014 | $H_2N$-YaFEII-T(beta-D-Glc)-amide |
| BBI-11015 | $H_2N$-YaFEVV-S(beta-D-Glc)-amide |
| BBI-11016 | $H_2N$-Dmt-aFE-Nle-Nle-T(beta-D-Glc)-amide |
| BBI-11017 | $H_2N$-Ya-Tic-E-Nle-Nle-T(beta-D-Glc)-amide |
| BBI-11018 | $H_2N$-YBFE-Nle-Nle-T(beta-D-Glc)-amide |
| BBI-11019 | $H_2N$-Tmt-aFE-Nle-Nle-T(beta-D-Glc)-amide |
| BBI-11020 | $H_2N$-Ya-Nmf-E-Nle-Nle-T(beta-D-Glc)-amide |

Amino Acids.

In addition to the above peptides, the present invention also includes peptides wherein one or more of the amino acids listed in Tables 1 through 5 is replaced by the corresponding D-enantiomer, or by a non-naturally occurring amino acid analog.

Note that the following common abbreviations are used for amino acids: Alanine=A or Ala; Arginine=Arg or R; Asparagine=N or Asn; Aspartic Acid=Asp or D; Cysteine=C or Cys; Glutamic Acid=Glu or E; Glutamine=Gln or Q; Glycine=Gly or G; Histidine=His or H; Isoleucine=Ile or I; Leucine=Leu or L; Lysine=Lys or K; Methionine=Met or M; Phenylalanine=Phe or F; Proline=Pro or P; Serine=Ser or S; Threonine=Thr or T; Tryptophan=Trp or W; Tyrosine=Tyr or Y; and Valine=Val or V. The D-enantiomer of an amino acid may be indicated by a small letter [e.g., 'a' for Alanine] or by the abbreviation "d" before the amino acid [e.g., dA or dAla].

Glycosylation.

Suitable sugar or saccharide moieties for attachment to the glycopeptides of the present invention may include both natural and synthetically made saccharides. In preferred embodiments, the saccharides useful in the present invention may include monosaccharides, disaccharides and oligosaccharides, including but not limited to the monosaccharides, dihydroxyacetone, glyceraldehydes, aldotriose, erythrulose, erythrose, threose, ribulose, psicose, xylose, glucose (Glc), fructose, mannose, galactose, fucose, ribose, tagatose, arabinose, rhamnose, sedoheptalose and nonoses such as neuraminic acid, sialic acid; the disaccharides sucrose, trehalose, saccharose, maltose, lactose (Lac), turanose, cellobiose, gentibiose, isomaltose, melibiose, and primeveose; oligosaccharides such as maltotriose, raffinose, melicitose, acarbose, stachyose, and oligofructose. In certain embodiments, the saccharide moieties useful in the present invention may include polysaccharides, such as inulin, fructan, glycogen, amylose, pectin, amylopectin, dextrin/dextran, betaglucans, maltodextrin, mannans, chitins, inositols, such as myo-inositol, inositol phosphates and inositol hexanicotinate and glycosaminoglycans, such as heparin, heparin sulfate and chondroitin sulfate.

Formulations.

The compositions of the present invention may further comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars; starches; cellulose and its derivatives; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable excipients which may be used in the manufacture of pharmaceutical compositions also include, but are not limited to, inert diluents, dispersing and/or granulating agents, surface active agents and/or emulsifiers, disintegrating agents, binding agents, preservatives (e.g., antioxidants, chelating agents, antimicrobial preservatives, antifungal preservatives, alcohol preservatives, acidic preservatives, and the like), buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

In certain embodiments, the composition further comprises one or more sugars. The term "sugar" as used herein refers to a natural or an unnatural monosaccharide, disaccharide, oligosaccharide, or polysaccharide, comprising one or more triose, tetrose, pentose, hexose, heptose, octose, or nonose saccharides. Sugars may include substances derived from saccharides by reduction of the carbonyl group (alditols), by oxidation of one or more terminal groups to carboxylic acids (aldonic acids), or by replacement of one or more hydroxyl group(s) by a hydrogen (deoxy sugars), an amino group (amino sugars), a thiol group (thio sugars), an acylamino group, a sulfate group, a phosphate group, or similar heteroatomic group; or any combination of the foregoing modifications. The term sugar also includes derivatives of these compounds (i.e., sugars that have been chemically modified by acylation, alkylation, and formation of glycosidic bonds by reaction of sugar alcohols with aldehydes or ketones, etc.). Sugars may be present in cyclic (oxiroses, oxetosesm furanoses, pyranoses, septanoses, octanoses, etc.)

form as hemiacetals, hemiketals, or lactones; or in acyclic form. The saccharides may be ketoses, aldoses, polyols and/or a mixture of ketoses, aldoses and polyols.

Exemplary sugars include, but are not limited to glycerol, polyvinylalcohol, propylene glycol, sorbitol, ribose, arabinose, xylose, lyxose, allose, altrose, mannose, mannitol, gulose, dextrose, idose, galactose, talose, glucose, fructose, dextrates, lactose, sucrose, starches (i.e., amylase and amylopectin), sodium starch glycolate, cellulose and cellulose derivatives (i.e., methylcellulose, hydroxypropyl cellulose, hydroxyethyl cellulose, hydroxyethylmethyl cellulose, carboxymethyl cellulose, cellulose acetate, cellulose acetate phthalate, croscarmellose, hypomellose, and hydroxypropyl methyl cellulose), carrageenan, cyclodextrins (e.g., hydroxypropyl-gamma-CD), dextrin, polydextrose, and trehalose. In certain embodiments, the sugar is selected from lactose anhydrous, lactose monohydrate, trehalose and hydroxypropyl-gamma-CD.

In certain embodiments, the composition further comprises one or more polymers. In certain preferred embodiments, the polymer is polyvinyl alcohol (PVA). Other Examples include gelatin, polyvinyl pyrolidone (PVP), albumin, and polyethyleneimine (PEI), acacia gum, cellulose derivatives, calcium polypectate, maleic anhydride derivatives, polyacrylic and methacrylic acid, phospholipids, polyglycolide and lactide derivatives, starch, alginates and alginic acid, calcium caseinate, carrageenan, pectins, polyhexametaphosphate, polyvinyl acetate, polyvinyl alcohol, and the like; mixtures thereof; and the like.

In certain embodiments, the composition further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite ($NaHSO_3$).

In certain embodiments, the one or more preservative comprises a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises an alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient (i.e., a glycosylated deltorphin variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

Preferred dosage forms include oral and parenteral dosage forms. Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases, Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. No. 5,912,014, U.S. Pat. No. 6,086,918 and U.S. Pat. No. 6,673, 574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in Remington: *The Science and Practice of Pharmacy* $21^{st}$ ed., Lippincott Williams & Wilkins, 2005.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits that comprise one or more inventive complexes and/or compositions. Kits are typically provided in a suitable container (e.g., for example, a glass, foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

The compositions and formulations of the present invention are useful for the treatment of conditions associated with the delta opioid receptor. Such conditions include, without limitation, the treatment of pain, including acute and chronic pain, nociceptic pain, cancer pain, neuralgia and myalgia. Other conditions treatable as part of the present invention include neurological disorders such as Parkinson's Disease, Alzheimer's Disease, Pick's Disease, and Chronic Fatigue Syndrome. The invention can also be used to treat emotional and mood disorders, such as depression, anxiety, addiction and obsessive compulsive disorder.

EXAMPLE 1

Synthesis and Purification of Glycopeptides

Briefly, acetate-protected glycosyl 9-fluorenylmethyloxy carbamate amino acids are synthesized using patented methods described in U.S. Pat. Nos. 5,470,949 and 5,767,254. Deprotection of the Schiff base glycoside esters and reprotection afford modified amino acid glycosides in excellent yield. Subsequent peptide synthesis utilizes deprotection with 30% piperidine in nonaqueous solution. Directed coupling reactions are sequential and proceed with over 98% yield per step. Additional protecting groups from the carbohydrate are removed while on a fixed resin. Cleavage from the resin is accomplished with no affect upon the glycosidic linkage of the peptide. After HPLC purification, glycopeptides are then characterized by $^1$H NMR, $^{13}$C NMR, correlation spectroscopy, total correlation spectroscopy, rotating frame nuclear Overhauser enhancement spectroscopy, and fast atom bombardment high-resolution mass spectroscopy. Using these procedures, a set of glycosylated deltorphin analogs is synthesized and purified. Each of these novel compounds is advanced into in vitro and in vivo bioassays.

EXAMPLE 2

Radioligand Binding Studies

The affinity and selectivity of glycosylated deltorphin analogs for the three canonical opioid receptors (MOR, DOR, and KOR-kappa) is determined biochemically using receptor binding assays. Membranes from Chinese Hamster Ovary (CHO) cells that stably express either the human mu, delta, or kappa opioid receptor are incubated with various concentrations of the drug to determine comparative inhibitory measurements and determination of receptor selectivity. Each of the novel compounds (15-20) are screened first for receptor affinity at the human DOR, MOR and Kappa opioid receptors (KOR). Those compounds which display moderate to high affinity (Ki<30 nM) and DOR selectivity (20-fold or greater over MOR) are assessed in the GTPγS assay (Example 3) in order to confirm functional agonist activity at the DOR target and are advanced to in vivo testing (Example 4).

Specific Methodology for Opioid Binding Studies is as Follows:

Membranes are isolated from CHO cells stably expressing human MOR, DOR, or KOR. At approximately 80% confluence, the cells are harvested by the use of a cell scraper and the cells and media from the plates are centrifuged at 200×g for 10 min at 4° C. Cells are resuspended in 50 mM Tris-HCl, pH 7.5, and are homogenized by the use of a Polytron. The membranes are centrifuged at 48,000×g for 20 min at 4° C. and then resuspended in 50 mM Tris-HCl, pH 7.5, at a protein concentration of 5-10 mg/ml, as determined by the Bradford method (Bradford, 1976), using bovine serum albumin as the standard and stored frozen at −80° C. until use. Cell membranes are incubated at 25° C. with the radiolabeled ligands in a final volume of 1 ml of 50 mM Tris-HCl, pH 7.5. Incubation times of 60 min are used for the MOR-selective peptide [3H]DAMGO and the KOR-selective ligand [3H]U69,593, and a 3-hr incubation are used with the DOR-selective antagonist [3H]naltrindole. Nonspecific binding is measured by inclusion of 10 μM naloxone. The binding is terminated by filtering the samples through Schleicher & Scheull No. 32 glass fiber filters using a Brandel 48-well cell harvester. The filters are subsequently washed three times with 3 ml of cold 50 mM Tris-HCl, pH 7.5, and will be counted in 2 ml of Ecoscint A scintillation fluid. For [3H]U69,593 binding, the filters are soaked in 0.1% polyethylenimine for at least 30 mM before use. IC50 values are calculated by least squares fit to a logarithm-probit analysis. Ki values of unlabeled compounds will be calculated from the equation Ki=(IC50)/1+S where S=(concentration of radioligand) (Kd of radioligand) (Cheng and Prusoff, 1973).

EXAMPLE 3

[$^{35}$S]GTPγS Binding Assay

Peptides having at least a 20-fold higher affinity for the DOR than for the MOR and KOR receptors, and having a Ki value of 10 nM or less at the DOR are tested in the [$^{35}$S] GTPγS binding assay to determine if the peptide is an agonist, antagonist, or partial agonist at the DOR. Membranes from the CHO cell lines, expressing either the MOR, DOR or KOR, will be incubated with 12 concentrations of each peptide for 60 min at 30° C. in a final volume of 0.5 mL of assay buffer (50 mM Tris-HCl, 3 mM MgCl2, 0.2 mM EGTA, 100 mM NaCl, pH 7.5) containing 3 μM GDP and 0.08 nM [$^{35}$S] GTPγS. Basal binding is determined in the presence of GDP and the absence of opioids, and nonspecific binding is determined by including 10 μM unlabeled [$^{35}$S] GTPγS. The incubation is terminated by filtration under vacuum through glass fiber filters, followed by three washes with 3-ml ice-cold 50 mM Tris-HCl, pH 7.5. Samples are allowed to equilibrate overnight and are counted in 2 ml of Ecoscint A scintillation fluid for 2 min in a liquid scintillation counter.

EXAMPLE 4

In Vivo Assessment of Opioid Glycopeptides

Compounds meeting the first set of criteria are screened initially for antinociceptive activity in the tail-flick assay following intracerebroventricular (icv) and intravenous (iv) routes of administration. This in vivo screening assay is sensitive to the activity of deltorphin-based peptides and is highly efficient and rapid in determining efficacy and relative potency of compounds (Bilsky et al., 1994, 2000). Testing and comparing glycosylated versus unglycosylated peptides at the two dosing routes determines the effects of glycosylation on CNS bioavailability and determines the relative potency of glycosylated compounds. In addition to efficacy, early-stage assessment of side effects is made by gross observation following dosing (e.g., locomotor stimulation and stereotypy, Straub tail/muscular rigidity, convulsions, etc.).

Acute Thermal Nociception Assay.

The 52° C. tail-flick assay (optimized for DOR agonist sensitivity) is used to detect in vivo opioid activity at the DOR receptor following icv and iv injection of glycopeptides (and unglycosylated parent peptides). This is a modified version of the classic tail-flick test developed by D'Amour and Smith in 1941 and is sensitive to the antinociceptive effects of deltorphin-based, DOR-selective, peptides. Mice are lightly but firmly grasped by the nape of the neck with the evaluator's thumb and fingers, and the distal half of the tail is then dipped into a bath of circulating, thermostatically controlled water. Latency to respond to the heat stimulus with vigorous flexion of the tail is measured to the nearest 0.1 s. A 10 sec cut-off is used to prevent tissue damage to the tail. Antinociception is calculated by the following formula: % Antinociception= [(Test Latency−Baseline Latency)/(10−Baseline Latency)]× 100. A baseline measurement will be taken and then each mouse will be injected at t=0 minutes. Mice are retested for antinociception at regular intervals (10, 20, 30, 45, 60, 90, 120 min) after the injection. An initial dosing of 10 nmol is used for compounds based on previous research with deltorphin peptides (Bilsky et al., 1995; 2000). If the animal displays minimal response (<20% MPE) at the 10-30 min time points, testing is terminated immediately after the 30 min time point. Doses are initially adjusted up or down in ½ log increments in an effort to generate a full dose response curve (3 doses with responses in the ~20-80% range). An upper limit of a 100 nmol (icv) or 32 mg/kg (iv) dose is put in place (or alternatively, if significant dose-limiting toxicity is observed). Compounds that elicit less than a 75% MPE at time of peak effect are not considered further for antinociceptive development, though the data is used to guide further design and synthesis efforts. Compounds that reach these criteria are advanced for further in vivo testing.

EXAMPLE 5

Assessment of Opioid Glycopeptide Effects Following Different Routes of Drug Administration For icv injections, mice are lightly anesthesized, and following an incision on the top of the skull, an icv injection is delivered 2 mm posterior to the bregma and 2 mm lateral to the midline. The injection is 3 mm deep from the skull to the lateral ventricle and a PE tubing cuff prohibits deeper injections to be made. Injection volume is kept constant at 5 ul/mouse. The mouse quickly (within 5 minutes) recovers from the anesthesia and is ready to be tested at the 10 min time-point. Mice are euthanized immediately after being tested. For iv injections, animals are briefly restrained in a Plexiglas holder and the distal portion of the tail is dipped into 42° C. warm-water for approximately 10 seconds to dilate the tail vein prior to injection. The icv and iv comparisons are important for determining potency ratios of the test compounds, as this provides a relative measure of blood brain barrier penetration with minimal confounds typically associated with other routes (e.g., gut absorption, first pass effects, etc.).

Compounds administered intravenously that elicit less than a 75% maximum possible effect (MPE) at time of peak effect are not considered appropriate for development as an antinociceptive product. Compounds which display potent and fully efficacious antinociceptive activity following both icv and iv administration are advanced to further assays and or formulated and tested for oral activity.

EXAMPLE 6

Assessment of Opioid Glycopeptides in a Sub-Acute Inflammatory Pain Model

Based upon results from the antinociceptive screening assay as well as behavioral observations, the most promising deltorphin-based glycopeptides are assessed for efficacy and potency in a commonly used, sub-acute inflammatory pain model: hind paw injection of complete Freund's adjuvant (CFA). Injection of CFA into the rodent hind-paw produces a strong inflammatory response that peaks between 24 and 48 hrs post-injection. This assesses the effects of systemic drug administration on paw volume, tactile thresholds and thermal response latencies before and after CFA administration. A key milestone is the observation of significant efficacy in the CFA model including potential anti-allodynic, anti-hyperalgesic and anti-inflammatory effects. Careful observation of animals is conducted to determine if there are any dose-limiting side effects associated with the compound. The CFA sub-acute model is used because it provides robust inflammatory pain efficacy data.

EXAMPLE 7

CFA Inflammatory Pain Model

For the CFA model, rats are baselined for tactile thresholds and thermal latencies (see below). Rats receive intradermal injections of 20 µl vehicle or CFA (1 mg/ml *Mycobacterium tuberculosis*, Sigma) solution into the plantar side of one hind paw. Rats are retested for tactile thresholds and thermal latencies at 24 hrs post-CFA/vehicle administration (a time where the effects of CFA are maximal). Complete dose- and time-response curves (n=6-8 rats/group) are completed with starting doses selected from data collected in the acute antinociceptive assays.

EXAMPLE 8

Thermal Latencies

Mice are habituated in Plexiglas chambers on a glass plate for ~45 minutes. A radiant heat source (Plantar™ Analgesia Instrument, Stoelting Co.) is applied to the middle of the plantar surface of each hind paw. The latency of the animal to lift its paw is recorded automatically. The intensity of the light is calibrated to produce baseline response latencies in control mice of ~10-12 seconds. Each evaluation is repeated twice (average taken) with an ~5-minute interval between determinations. A cut-off time of 20 seconds is used to avoid tissue damage to the hind paw.

EXAMPLE 9

Paw-Withdrawal Thresholds

Tactile thresholds are determined by probing the hindpaw of the mouse with a series of finely calibrated von Frey filaments (Stoelting Co.). The strength of the von Frey stimuli ranges from 0.02 g to 6 g on a logarithmic scale. Mice are allowed to acclimate within Plexiglas enclosures that have mesh bottoms for ~30 min, and then withdrawal thresholds are determined by increasing and decreasing stimulus strength until the minimal stimulus required to elicit a response is determined ("up-down" method). The paw-withdrawal threshold is estimated by the Dixon nonparametric test. The data are represented as mean withdrawal threshold±S.E.M. Paw-withdrawal baseline thresholds average ~4.5±0.5 g and are maintained in the non-injured controls at approximately this level across repeated testing.

EXAMPLE 10

Osteoarthritis Model

An osteoarthritis pain model is utilized for several reasons. First, osteoarthritis represents a major chronic pain condition that has a significant health and economic burden, and for which current pharmacotherapies either lack adequate efficacy and/or are limited by side effects. Second, there are a number of well-characterized osteoarthritis pain models in rodents including the intraarticular injection of sodium iodoacetate into the knee joint. And third, enkephalin and dynorphin systems (DOR, as well MOR and KOR) are dynamically regulated in the pathology of arthritis.

Animals are first base-lined for mechanical thresholds or differential weight bearing (see below). For induction of arthritis, the animals are lightly anesthetized and administered an intraarticular injection of vehicle (0.9% NaCl) or sodium iodoacetate (1 mg in 25 μl) into the right knee. Animals are reassessed for mechanical thresholds or differential weight bearing on post-injection days 3, 7 and 21. For weight-bearing measurements, animals are habituated to the apparatus (Columbus Instruments Incapacitance Tester). The holder helps align the hind paws onto the two independent scales, and if needed the paws can be gently prodded so that separate readings are taken for differential weight bearing. The apparatus is programmed to take automatic readings (each averaged over 5 seconds), with three readings averaged to give the mean for baseline and each of the time-points.

EXAMPLE 11

Measuring Efficacy and Side Effects Using Animal Models

Data in the CFA model of inflammatory pain and the iodoacetate model of osteoarthritis pain is obtained in rats. These well-validated inflammatory pain models are used to assess compound potency and efficacy.

EXAMPLE 12

Locomotor Activity and Assays of Behavior and Side Effects

Assays are known whereby the degree to which an animal experiences pain, physical impairment, and other behavioral aspects can be measured. For example, see PCT Patent Application WO 05/114181, See also, the SCANET MV-10 metabolism measuring system described for example, in Taniguchi et al., Evid Based Complement Alternat Med., 1:187-191 (2004). The disclosure of these documents is hereby incorporated herein by reference.

EXAMPLE 13

Peptide Receptor Binding Experiments

The following peptides were prepared and tested in these experiments:

| | |
|---|---|
| 11001 = Deltorphin A1 | H2N-YmFHLMS(beta-D-Glc)-amide |
| 11002 = Deltorphin A2 | H2N-YaFHLAS(beta-D-Glc)-amide |
| 11003 = Deltorphin A3 | H2N-YmFHLMT(beta-D-Glc)-amide |
| 11004 = Deltorphin A4 | H2N-YaFHLAT(beta-D-Glc)-amide |
| 11005 = Deltorphin B1 | H2N-YaFE-Nva-Nva-S(beta-D-Glc)-amide |
| 11006 = Deltorphin B2 | H2N-YaFE-Nle-Nle-S(beta-D-Glc)-amide |
| 11007 = Deltorphin B3 | H2N-YaFE-Nva-Nva-T(beta-D-Glc)-amide |
| 11008 = Deltorphin B4 | H2N-YaFE-Nle-Nle-T(beta-D-Glc)-amide [SEQ ID NO: 31] |

The above peptides were tested at 100 nM and 1 nM vs. 0.2 nM [3H]Naltrindole binding to 20 ug hDOR CHO cell membranes. The experiments were performed with two racks filtered separately, but using the same [3H]Naltrindole stock solution, membranes and buffer. Non-specific binding was measured in the presence of 100 uM naloxone. Non-specific binding was subtracted from the control and peptide total CPM to give specific CPM.

Figure 2:
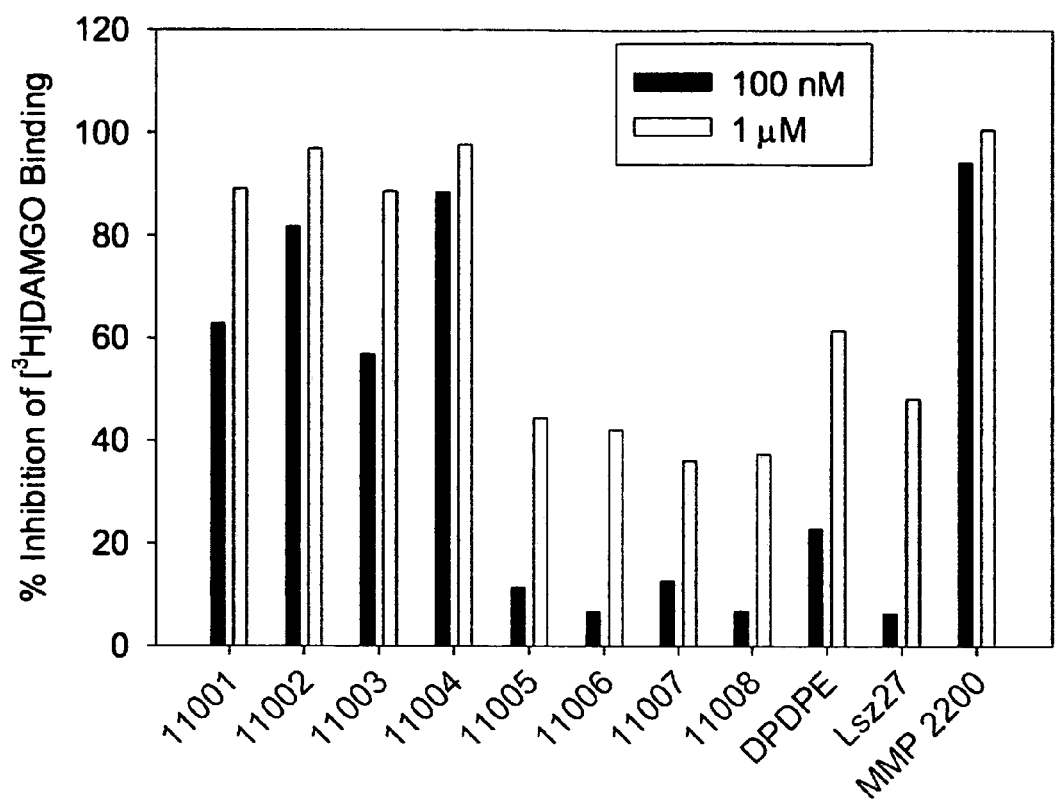
FIG. 2 illustrates the % inhibition of tritium-labeled DAMGO binding by glycopeptides 11001 through 11008, compared with DPDPE, Lsz27 and MMP2200.

The results for delta and mu receptor binding are illustrated in FIGS. 1, and 2, respectively. The data of FIGS. 1 and 2 indicate that the rank order of affinity for the delta receptor is:

[11001≈111003≈11008≈DPDDE]>
    [11005≈11006≈11007]>[11002≈11004]>Lsz27

Pharmacology.

Of the 8 peptides synthesized and screened as described above, two (11008 and 11005) were selected for testing across a range of concentrations at all three opioid receptors. Full binding curves at delta, mu and kappa were completed and the binding data for 11008 and 11005 are presented below.

Methods:

Briefly, the peptides were tested in competition binding experiments across a wide range (0.1 nM to 10 μM) of 12 different concentrations to determine the relative affinity of the peptides for the delta, mu and kappa opioid receptors. Based on the results from the initial set of experiments, the concentration range was then narrowed so that at least 8 datum points fell on the descending portion of the inhibition curve. Compounds were tested in triplicate. Membranes from Chinese hamster ovary cells with stably expressed delta, mu or kappa opioid receptors were used. The delta-selective antagonist [$^3$H]naltrindole was used at a final concentration of 0.2 nM, the mu-selective peptide agonist [$^3$H]DAMGO was used at a final concentration of 0.25 nM and the kappa-selective agonist, [$^3$H]U69,593. Nonspecific binding was measure in the presence of 100 μM naloxone. Twelve different concentrations of the peptides were used to determine the 1050 value for the delta and mu receptors, which was converted into a Ki value±S.E.M. For the kappa binding experiment, three subsequent tests were performed with the peptides at a final concentration of 10 μM to determine the percent inhibition of [$^3$H]U69,593 binding. Data for peptides 11008 and 11005 are summarized in Tables 7 and 8, respectively.

TABLE 7

[$^3$H] Binding Summary for 11008 in hDOR, hMOR and hKOR CHO Cell Membranes

| | Delta [$^3$H]Naltrindole | | Mu [$^3$H]DAMGO | | Kappa [$^3$H]U69,593 | |
|---|---|---|---|---|---|---|
| | Mean | SEM | Mean | SEM | Mean | Sem |
| IC50 (nM) | 42 | 1.1 | 1500 | 19 | NA | NA |
| $K_i$ (nM) | 14 | 0.34 | 1100 | 13 | NA | NA |

TABLE 7-continued

[$^3$H] Binding Summary for 11008 in hDOR,
hMOR and hKOR CHO Cell Membranes

|  | Delta [$^3$H]Naltrindole | | Mu [$^3$H]DAMGO | | Kappa [$^3$H]U69,593 | |
|---|---|---|---|---|---|---|
|  | Mean | SEM | Mean | SEM | Mean | Sem |
| Max Inhib at 10 uM (%) | NA | NA | NA | NA | 2.9% | 1.7% |

TABLE 8

[$^3$H] Binding Summary for 11005 in hDOR,
hMOR and hKOR CHO Cell Membranes

|  | Delta [$^3$H]Naltrindole | | Mu [$^3$H]DAMGO | | Kappa [$^3$H]U69,593 | |
|---|---|---|---|---|---|---|
|  | Mean | SEM | Mean | SEM | Mean | Sem |
| IC50 (nM) | 61 | 5.4 | 1000 | 4.6 | NA | NA |
| K$_i$ (nM) | 20 | 1.8 | 710 | 3.2 | NA | NA |
| Max Inhib at 10 uM (%) | NA | NA | NA | NA | 5.3% | 1.9% |

As shown in the summary tables above, 11008 has a lower IC50 (42 nM) and Ki (14 nM) at the delta receptor than 11005 (61 nM and 20 nM, respectively). 11008 has a higher IC50 and Ki at the mu receptor and less maximum inhibition at kappa than 11005.

Figure 3:
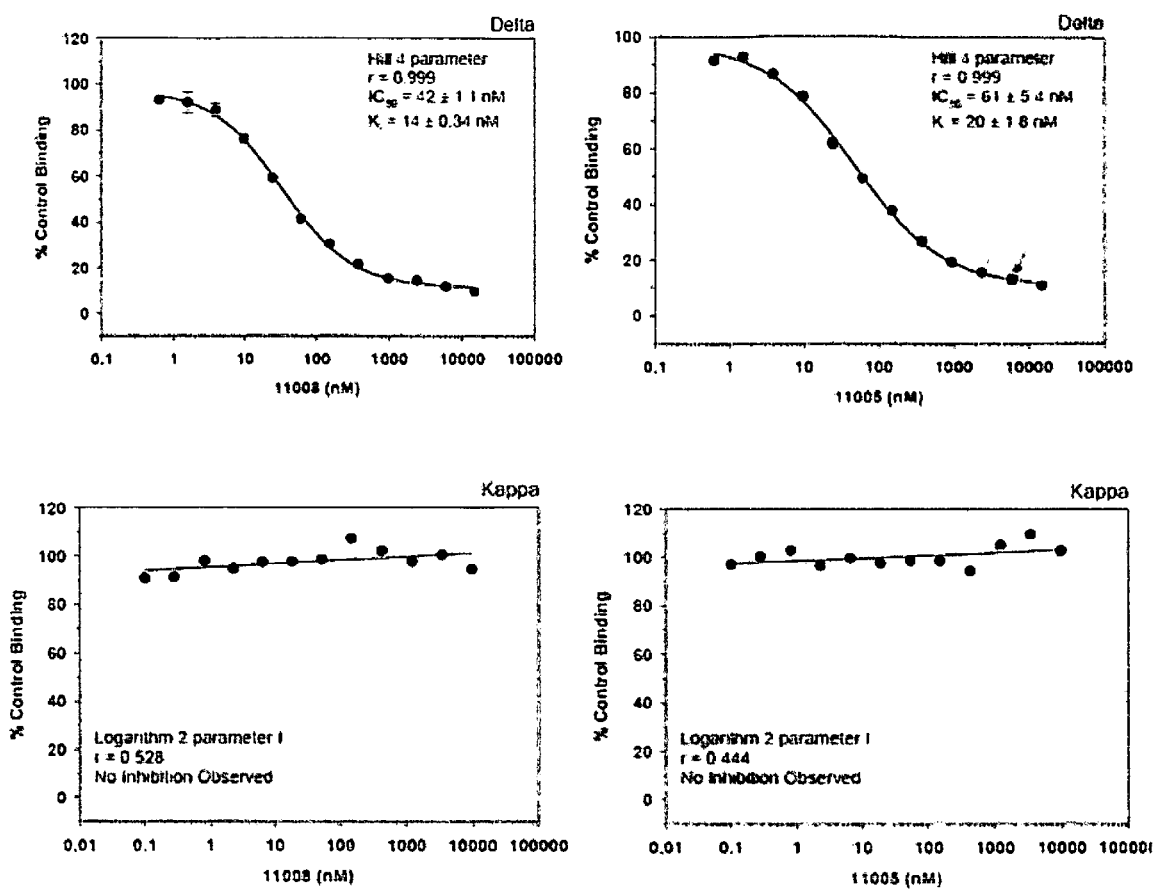
FIG. 3 illustrates the % of control binding to the Delta, Mu and Kappa opioid receptors, by glycopeptides 11008 and 11005, respectively.

The full binding curves for the two peptides at each receptor are shown in FIG. 3, and a summary of affinity and selectivity data is provided in Table 9. Results of the binding studies indicate that 11008 has somewhat greater affinity and selectivity for the delta receptor than 11005. Also, although 11008 has approximately a 3-fold lower affinity for delta than DPDPE, the compound has greater selectivity for the delta receptor relative to mu than DPDPE. The selectivity of 11008 for delta (1:79 delta:mu) is highly selective compared to LSZ27 and DPDDE.

TABLE 9

Summary of Affinity and Selectivity for
Peptides 11008, 11009, LSZ27 and DPDPE

| Peptide | Delta [$^3$H]Naltrindole | | Mu [$^3$H]DAMGO | | Kappa [$^3$H]U69,593 | | Selectivity Delta:Mu |
|---|---|---|---|---|---|---|---|
|  | Mean | SEM | Mean | SEM | Mean | Sem |  |
| 11008 | 14 | 0.34 | 1100 | 13 | NA | NA | 1:79 |
| 11005 | 20 | 1.8 | 710 | 3.2 | NA | NA | 1:36 |
| LSZ27 | 33 | 2.5 | 570 | 44 | NA | NA | 1:17 |
| DPDDE | 4.3 | 0.48 | 180 | 7.2 | NA | NA | 1:42 |

Results of [$^{35}$S]GTPγS Binding Summary for 11008 and 11009 in hMOR, hKOR, and hDOR CHO Cell Membranes.

Peptide 11008 (H2N-YaFE-Nle-Nle-T(beta-D-Glc)-amide) and 11009 (H$_2$N-YaFE-Nle-Nle-T-amide) were synthesized and tested in accordance with the [$^{35}$S] GTPγS binding assay described in Example 3. Results are summarized in Table 10 and 11:

TABLE 10

[35S]GTPγS Binding Summary for 11008 in
hMOR, hKOR, and hDOR CHO Cell Membranes

| Properties: | Delta | | Mu | | Kappa | |
|---|---|---|---|---|---|---|
|  | Mean | SEM | Mean | SEM | Mean | SEM |
| Agonist Properties | | | | | | |
| EC50 (nM) | 12 | 3.1 | NA | NA | NT | NT |
| EMax (%) | 75 | 3.0 | 27% @ 10 um | 2.9 | NT | NT |
| Antagonist Properties | | | | | | |
| IC50 (nM) | NA | NA | NA | NA | NT | NT |
| Imax (%) | No Inhibition | No inhibition | No Inhibition | No inhibition | NT | NT |
| Description: | Agonist | | Very weak agonist | | NA | |

TABLE 11

[35S]GTPγS Binding Summary for 11009 in
hMOR, hKOR, and hDOR CHO Cell Membranes

| Properties: | Delta | | Mu | | Kappa | |
|---|---|---|---|---|---|---|
|  | Mean | SEM | Mean | SEM | Mean | SEM |
| Agonist Properties | | | | | | |
| EC50 (nM) | 12 | 3.7 | NA | NA | NT | NT |
| EMax (%) | 67 | 4.5 | 42% @ 10 um | 2.4 | NT | NT |
| Antagonist Properties | | | | | | |
| IC50 (nM) | NA | NA | NA | NA | NT | NT |
| Imax (%) | No Inhibition | No inhibition | No Inhibition | No inhibition | NT | NT |
| Description: | Agonist | | Very weak agonist | | NA | |

Oral Availability of Formulations

Oral formulations of glycopeptide 11008 were prepared in accordance with the present specification and were compared with saline formulations of glycopeptide 11008 in the mouse tail flick assay. Formulated at 32 mg/kg, glycopeptide 11008 produced 75% antinociceptive activity compared with 30% for the saline formulation. The oral formulation at 3.2 mg/kg produced just slightly lower efficacy than that produced by 32 mg/kg of unformulated glycopeptide 11008.

While the present invention has been has been described with respect to specific embodiments thereof, it will be evident to those skilled in the art that various modifications and changes may be made thereto without departing from the essential spirit and scope of the invention. Accordingly, the compositions and methods comprising such modifications and changes constitute part of the present invention.

LIST OF REFERENCES

Aceto et al., 2007; *European Journal of Pharmacology*, 566: 88-93
Bilsky et al.; *J Med Chem*. (2000); 43:2586-2590.
Brainin-Mattos et al., 2006; *Pain;* 122:174-181
Cahill et al., 2003 *Brain Research,* 960:209-218
Calderon et al., 1994; 2004; *Regulatory Peptides, Volume* 54:45-46;
Cheng et al. (1993) *European Journal of Pharmacology*, 230: 85-88
Cheng and Prusoff 1973 Biochem. Pharm, 22:3099-3108

Dhanasekaran and Polt; Curr Drug Deliv. 2005 2:59-73
Do Como et al., *J Pharmacol Exp Ther.* (2008) 326: 939-948.
Do Como et al., *Pain*, 2009; 144:170-177
Dolle et al., *Bioorganic & Medicinal Chemistry Letters*, 17:2656-2660 (2007)
Egleton et al., *Tetrahedron: Asymmetry*, 2005 16:65-75
Egleton et al., J Pharmacol Exp Ther. 2001 299:967-72
Egleton et al., Brain Res. 2000 881:37-46
Elmagbari et al., 2004; J Pharmacol Exp Ther. 311:290-7
Franck et al., 1991 *Brain Research*, 563:123-126
Fraser et al., 2000; *Life Sciences*, 67:913-922
Gallantine and Meert; *Pharmacology Biochemistry and Behavior;* 79:125-135
Gavériaux-Ruff et al., 2008; *Biological Psychiatry*, 63:633-636
Holdridge & Cahill, 2007; *European Journal of Pain*, 11:685-693
Jutkiewicz, 2006; *European Journal of Pharmacology*, 531: 151-159
Kreil et al., 1989; *European Journal of Pharmacology*, 162: 123-128
Lazarus et al., *Progress in Neurobiology* (1999); 57:377-420.
Keyari et al., Adv Exp Med Biol. 2009; 611:495-6
Lord et al., 1977, Nature 267:495.
Lowery et al., 2007, Chem Biol Drug Des. 69:41-7
Mercer et al., *Journal of Pain*, 2008 9 Supp 2:5
Mika et al., 2001 *European Journal of Pharmacology*, 415: 31-37
Mosberg et al., 1983 *Proc Natl Acad Sci USA*. 1983 80(: 5871-5874.
Moulin et al., 1985 *Can Med Assoc J.* 1985 133: 546.
Nadal et al., 2006; *Brain Research*, 1094:1-12
Negri et al., Eur. J. Pharmacol. 1996; 296:9-16.
Negri et al., (1999) J. Med. Chem. 42:400-404
Onofrio & Yaksh, 1983; *Lancet*, 321:1386-1387
Polt et al.; *Proc Natl Acad Sci USA*. (1994) 91: 7114-7118
Polt et al. 2005; Med Res Rev. 25:557-85
Solá et al., 2007; Cell Mol Life Sci. 64:2133-52
Stevenson et al., J Pain. 7:408-16 (2006)
Stevenson et al., Life Sci., 85:309-15 (2009).
Strange 1980; *Endeavour,* 4:128
Su et al., 1998; J Neurophysiol. 80:3112-9
Susaki et al., 1999 Biol Pharm Bull; 22:1094-8
Tancredi et al., 1991; Biopolymers; 31:751-60.
Tomatis et al., 1997 J. Med. Chem. 40:2948-2952.
Torregrossa et al., 2006; *Brain Research,* 1069:172-181
Uberti et al., *Peptides*, (1985) Vol. 6, Supp 3:171-175
Vankova et al. 1996 *Neuroscience, Volume* 74:219-235
Walwyn et al., 2006 Neuroscience; 142:493-503
Walwyn et al., 2005; Mol Pharmacol; 68:1688-98
Walwyn et al., 2004; *Neuroscience,* 123: 111-121

All publications that are referenced within the present specification are hereby incorporated herein by reference for the disclosure and teachings provided in such publications.

The invention claimed is:

1. A glycosylated peptide consisting essentially of an amino acid sequence:

X1-X2-X3-X4-X5-X6-X7-NH2 (SEQ ID NO: 30)

wherein:
X1 is Y;
X2 is dAla;
X3 is F;
X4 is E;
X5 and X6 each are Nle or Nva; and
X7 is selected from Thr, dThr, Ser, or dSer; and wherein X7 is glycosylated with beta-D-Glc.

2. The glycosylated peptide of claim 1, consisting essentially of the amino acid sequence: Y-dAla-F-E-Nle-Nle-Thr (beta-D-Glc)NH2 (SEQ ID NO: 31).

3. The glycosylated peptide of claim 1, consisting essentially of the amino acid sequence: Y-dAla-F-E-Nva-Nva-Ser (beta-D-Glc)NH2 (SEQ ID NO: 9).

4. The glycosylated peptide of claim 1, consisting essentially of the amino acid sequence: Y-dAla-F-E-Nle-Nle-dThr (beta-D-Glc)NH2 (SEQ ID NO: 17).

5. The glycosylated peptide of claim 1, consisting essentially of the amino acid sequence: Y-dAla-F-E-Nle-Nle-dSer (beta-D-Glc)NH2 (SEQ ID NO: 18).

6. A method of treating a subject suffering from a neurological disease or disorder, comprising administering the glycosylated peptide of claim 1 to the subject.

7. A method of treating a subject suffering from a neurological disease or disorder, comprising administering the glycosylated peptide of claim 2 to the subject.

8. A method of treating a subject suffering from a neurological disease or disorder, comprising administering the glycosylated peptide of claim 3 to the subject.

9. A method of treating a subject suffering from a neurological disease or disorder, comprising administering the glycosylated peptide of claim 4 to the subject.

10. A method of treating a subject suffering from a neurological disease or disorder, comprising administering the glycosylated peptide of claim 5 to the subject.

11. The method of claim 6, wherein the neurological disease or disorder involves acute or nociceptive pain.

* * * * *